United States Patent [19]

Pacifici et al.

[11] 4,095,939

[45] Jun. 20, 1978

[54] OPTICALLY BRIGHTENED POLYESTERS WITH 2,5-BIS-(P-CARBOALKYLSTYRYL)-OXADIAZOLE

[75] Inventors: James G. Pacifici; Richard H. S. Wang, both of Kingsport, Tenn.

[73] Assignee: Eastman Kodak Company, Rochester, N.Y.

[21] Appl. No.: 794,858

[22] Filed: May 9, 1977

[51] Int. Cl.$^2$ .................... D06P 1/38; C09K 11/00
[52] U.S. Cl. ............................ 8/1 W; 8/179; 252/301.28; 260/307 G
[58] Field of Search ................ 8/1 W; 252/301.28

[56] References Cited

U.S. PATENT DOCUMENTS 3,963,738   6/1976   Irick et al. .................... 260/307 G

FOREIGN PATENT DOCUMENTS 932,184   7/1955   Germany.
896,219   5/1962   United Kingdom.

OTHER PUBLICATIONS

Venkataraman, K., "The Chemistry of Synthetic Dyes," vol. V, (Academic Press, 1971), p. 657.

Primary Examiner—A. Lionel Clingman
Attorney, Agent, or Firm—Donald W. Spurrell; Daniel B. Reece, III

[57] ABSTRACT

This invention concerns optically brightened polyester materials and, in particular, formed polyester articles such as fibers containing certain 2,5-bis(p-carboalkoxystyryl)oxadiazole compounds such as 2,5-bis(4'-carbomethoxystyryl)-1,3,4-oxadiazole. These compounds impart exceptional brightness to the polyester and themselves have good fastness and stability properties.

3 Claims, No Drawings

OPTICALLY BRIGHTENED POLYESTERS WITH 2,5-BIS-(P-CARBOALKYLSTYRYL)-OXADIAZOLE

This invention concerns optically brightened polyester materials and, in particular, formed polyester articles such as fibers containing certain 2,5-bis(p-carboalkoxystyryl)oxadiazole compounds. These compounds impart exceptional brightness to the polyester and themselves have good fastness properties.

Optical brighteners by necessity must be peculiarly accommodating. Their primary and unusual ability to continuously absorb non-visible excitation energy and then dynamically convert the same to the visible region is singularly impressive particularly should this capacity also be acceptable visually in the apparel fiber field. Even more impressive, however, are such brighteners which themselves also exhibit good fastness properties to conditions of light, wash, dry cleaning, dyeing process, sizing, hot ironing, chemical, pH, and the like, and which do not sensitize or otherwise induce or contribute to degradation of the substrate.

The brightener compounds of this invention are quite remarkable in their ability to satisfy most if not all of the aforesaid desirable conditions, particularly on fibers of polyesters such as those based on poly(ethylene terephthalate) known by the tradenames Kodel, Dacron, Anavor, Avlin, Fortrel, Quintess, Spectran and Trevira. The present brighteners are selected from 2,5-bis(p-carboalkoxystyryl)-1,3,4-oxadiazoles having the general formula

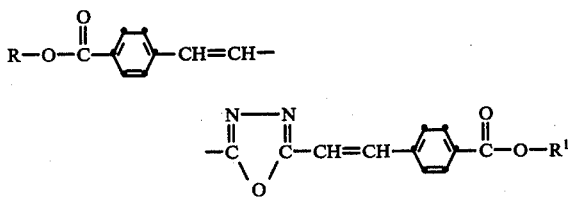

wherein R and R¹ are independently selected from alkyl of 1-12 carbons such as methyl, ethyl, propyl, isopropyl, butyl and hexyl; cycloalkyl of 5-10 carbons such as cyclohexyl and cyclopentyl; alkyl of 1-10 carbons substituted with —OH, alkoxy of 1-6 carbons, Cl, Br, alkylamino of 1-6 carbons, such as 2-chloroethyl, 2-hydroxyethyl, 2-methoxyethoxy and 2-dimethylamino ethyl, and with cycloalkyl such as cyclohexyl and cyclopentyl. The compounds wherein R and R¹ are alkyl of 1-4 carbons are highly preferred and the most preferred compound has R and R¹ both methyl.

2,5-Disubstituted oxadiazoles such as 2,5-diphenyl-1,3,4-oxadiazole described in Swiss Patent 383,985 and British Patent 896,219 are ineffective as brighteners in that they have inadequate fluorescence in the visible spectral region. The unsubstituted bis 2,5-styryloxadiazoles have been described in British Patent 896,219 as being useful as brighteners; however, as shown by Example 2 below, the presence of a carboalkoxy group at the 4 position in the styryl group when incorporated in polyester fibers results in unexpected and greatly superior fiber brightness.

The compositions of this invention are polyester substrates, particularly fibers, containing as little as 0.001% and preferably up to about 5.0% by weight of at least one of the above 2,5-bis(p-carboalkoxystyryl)-1,3,4-oxadiazoles, although higher concentrations may be employed. For most practical purposes, an amount ranging from 0.01% to 0.5% by weight of the fiber is preferred.

These compositions can be prepared by incorporating the brightener into the substrate material before or during forming into fibers. For example, the brightener may be dissolved, dispersed or in any other way finely distributed in the polymer mass before forming (spinning); or added to the starting materials, reaction mixtures or intermediate products used to prepare the fiber forming polymer. These compositions may also be prepared by treating the fiber with an aqueous dispersion or an organic solution of the brightener material.

The polyesters to which the present invention is applicable are those such as poly(ethylene terephthalate), poly(1,4-cyclohexylene dimethylene terephthalate) and modifications of such polymers with various aliphatic acids such as azelaic, and with aromatic acids such as isophthalic, and with various glycols such as diethylene glycol, polyoxyethylene glycols, and the like. Such polyesters usually have an I.V. of from about 0.25 to about 1.0 or above when employed as fiber material.

EXAMPLE 1

Following is the preparation of 2,5-bis(4'-carbomethoxystyryl)-1,3,4-oxadiazole which procedure is generally applicable to the preparation of the present brighteners:

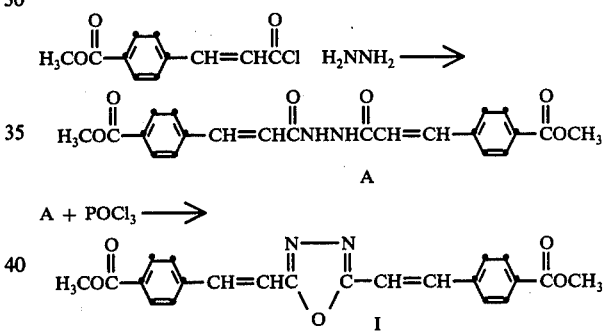

To a solution of hydrazine monohydrate (0.025 mole) and sodium bicarbonate (0.05 mole) in 100 ml of water, 4-carbomethoxycinnamoyl chloride (0.05 mole) in 100 ml of tetrahydrofuran was added slowly with stirring. After stirring for an additional 30 min., the intermediate A was filtered off and washed with 1 liter of water. The product has a mp >300° C., and yield of 95%. A solution of A (0.026 mole) and 40 ml of phosphorus oxychloride in 10 ml of toluene was refluxed for 6 hr. The product I was filtered and washed with water. The product had a mp of 270°–272° C., and yield of 90%.

EXAMPLE 2

Spectral and Emission Properties -

| | |
|---|---|
| $\lambda_{max}$ in CH$_2$Cl$_2$ | = 343 nm (Coleman - Hitachi Model 124 spectrophotometer) |
| $\epsilon$(M$^{-1}$cm$^{-1}$) | = 44,600 |
| Emission max | = 420 shoulder at 440 nm |
| Emission Intensity (Relative) | = 80 |

-continued

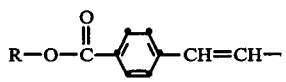

| | |
|---|---|
| $\lambda_{max}$ in $CH_2Cl_2$ | = 320 nm |
| $\epsilon(M^{-1}cm^{-1})$ | = 34,500 |
| Emission max | = 405 shoulder at 425 nm |
| Emission Intensity (Relative) | = 10 |

Quantitative comparison of the relative emission intensity was obtained employing an Aminco Bowman Spectrofluorometer. Solution samples of I and II, approximately $10^{-5}M$ in $CH_2Cl_2$, were adjusted as to concentration such that the absorbance of each solution at 350 nm (excitation wavelength) was the same. The carbomethoxy group significantly increases the fluorescence (emission) intensity of the styryl oxadiazoles. The difference in brightening power is readily observed also in a polyester film of approximately 1.0 mil thickness. Samples of poly(ethylene terephthalate) containing 200 ppm of I were significantly brighter than those containing 200 ppm of II.

EXAMPLE 3

Photostability - Samples (5.0 ml) of I (2.2 × $10^{-4}M$) and II (4.6 × $10^{-4}M$) in methylene chloride were irradiated in air in a 3100 A Rayonet Reactor (The Southern New England Ultraviolet Co.). The rate of photoreaction was determined by measuring the loss in optical density at the absorption maximum of each compound. Compound I had a rate of 0.65 × $10^{-7}$ moles/min. and Compound II had a rate of 3.5 × $10^{-7}$ moles/min. This difference in photostability between compound I and compound II was also observed in a polymer matrix.

Films of a polyester of a 50/50 acid mole ratio of terephthalic acid/isophthalic acid, and 1,4-cyclohexanediol, cast from methylene chloride and containing approximately 0.02% by weight of each of I and II, were exposed to a Gates 100-watt mercury lamp in air. Part of the film was covered with aluminum foil and part exposed to the light. After 1 hr. exposure, the sample containing II showed a significant break in fluorescence intensity whereas, the sample containing I remained unchanged.

EXAMPLE 4

Poly(ethylene terephthalate) woven test fabrics were treated with a methylene chloride solution of I and II. The initial concentrations of I and II in the methylene chloride were adjusted so that the fabrics which were treated had approximately the same fluorescence when exposed to U.V. light. These brightened fabrics, mounted in fading test masks, were exposed to a 100-watt mercury lamp. After 1 hr. exposure, samples containing II showed an appreciable loss in fluorescence, whereas, sample containing I showed no break.

The invention has been described in detail with particular reference to preferred embodiments thereof, but it will be understood that variations and modifications can be effected within the spirit and scope of the invention.

We claim:

1. Polyester material containing from about 0.001% to about 5.0% by weight of at least one compound of the formula

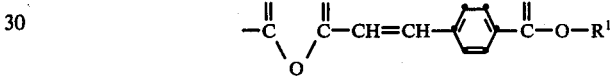

wherein R and $R^1$ are independently selected from alkyl of 1-12 carbons, cycloalkyl of 5-10 carbons, and alkyl of 1-10 carbons substituted with one or more of —OH, alkoxy of 1-6 carbons, Cl, Br, alkylamino of 1-6 carbons and cycloalkyl of 5-10 carbons.

2. Polyester fiber containing from about 0.01% to about 0.5% by weight of at least one compound of claim 1 wherein R and $R^1$ are selected from alkyl of 1-4 carbons.

3. The fiber of claim 2 wherein R and $R^1$ are each methyl.

* * * * *